(12) United States Patent
Hull et al.

(10) Patent No.: US 6,178,344 B1
(45) Date of Patent: Jan. 23, 2001

(54) RECONFIGURABLE ARRAY FOR POSITIONING MEDICAL SENSORS

(75) Inventors: Andrew J. Hull, Middletown, RI (US); Norman L. Owsley, Gales Ferry, CT (US)

(73) Assignee: The United States of America as represented by the Secretary of the Navy, Washington, DC (US)

( * ) Notice: Under 35 U.S.C. 154(b), the term of this patent shall be extended for 0 days.

(21) Appl. No.: 09/267,903

(22) Filed: Mar. 2, 1999

(51) Int. Cl.[7] .............................. A61B 5/04; A61B 5/103
(52) U.S. Cl. .................... 600/407; 600/382; 600/386; 600/393; 600/587; 600/595
(58) Field of Search .................... 600/407, 382, 600/383–387, 389, 393, 547, 587, 595, 529, 532, 534, 552–553

(56) References Cited

U.S. PATENT DOCUMENTS

| | | | | |
|---|---|---|---|---|
| 2,549,836 | * | 4/1951 | McIntyre et al. | 600/383 |
| 3,476,104 | * | 11/1969 | Davis | 600/393 |
| 3,483,861 | * | 12/1969 | Tiep | 600/534 |
| 3,490,439 | * | 1/1970 | Rolston | 600/383 |
| 3,957,037 | * | 5/1976 | Fletcher et al. | 600/384 |
| 4,151,836 | * | 5/1979 | Arnaud et al. | 600/382 |
| 4,202,344 | * | 5/1980 | Mills et al. | 600/382 |
| 4,308,870 | * | 1/1982 | Arkans | 600/382 |
| 4,437,468 | * | 3/1984 | Sorenson et al. | 600/459 |
| 4,517,983 | * | 5/1985 | Toyosu et al. | 600/386 |
| 4,573,474 | * | 3/1986 | Scibetta | 600/382 |

* cited by examiner

*Primary Examiner*—Joseph Pelham
(74) *Attorney, Agent, or Firm*—Michael J. Mcgowan; James M. Kasischke; Prithvi C. Lall

(57) ABSTRACT

A device for noninvasively measuring energy emissions in the human chest. This device includes first and second spaced longitudinal flexible supports. At least one transverse support means extends between the said first and second spaced longitudinal supports. A plurality of sensor means positioned in a spaced transverse array on the transverse support. This device is an array based measurement system that minimizes the effect of rib interaction on the space-time field of the human thorax. This array-based measurement system is noninvasive so there is almost no patient risk.

9 Claims, 1 Drawing Sheet

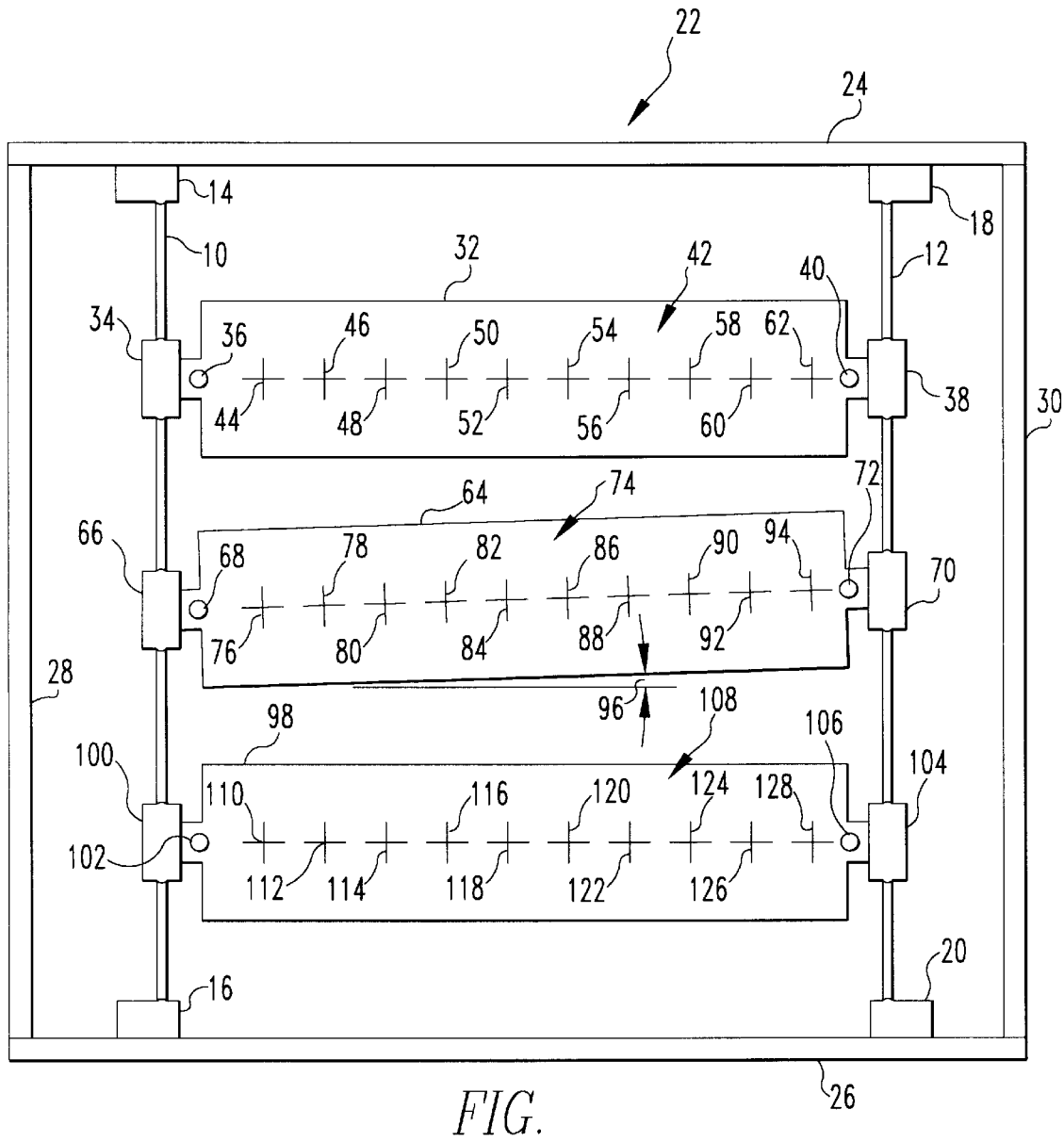
FIG.

RECONFIGURABLE ARRAY FOR POSITIONING MEDICAL SENSORS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION (1) Field of the Invention

The present invention relates to medical devices and more particularly to medical devices for noninvasive diagnostic measurement of the human body.

(2) Brief Description of the Prior Art

Various devices are known for providing noninvasive diagnostic measurements on the human body.

U.S. Pat. No. 4,295,471 to Kaspari, for example, discloses an apparatus for noninvasively monitoring arterial waveforms, such as the waveform produced by blood flow through the brachial artery in a human subject. The apparatus includes a transducer which senses both a pressure wave proportional to blood flow in the artery and an acoustical signal through a partially occluded artery.

U.S. Pat. No. 4,437,468 to Sorenson et al. discloses an ultrasound scanning system particularly adapted for scanning large body areas such as the back. There is a plurality of ultrasound transducers, each mounted in a transducer shoe, and each shoe in turn mounted on a plunger which seats in the bore of a housing so that it is free to move independently from the other transducers in a direction parallel to the bore, but is constrained to move with the other transducers in the two perpendicular directions. A spring seated in the bore between the housing and the plunger provides a bias force to maintain a positive and uniform contact between the transducer and the back.

U.S. Pat. No. 4,580,574 to Gavish discloses an ultrasound device for continuously and noninvasively monitoring instantaneous fluctuations in viscoelastic-related properties of tissue comprising a pair of substantially parallel spaced-apart piezoelectric transducers having a gap therebetween and adapted to bracket and come in direct contact with living tissue inserted in the gap between the transducers, at least one of the transducers being adjustable with respect to the other transducer whereby the distance between the transducers is adjustable to enable insertion and clamping of a segment of living tissue therein.

U.S. Pat. No. 4,836,212 to Schmitt et al. discloses a measuring apparatus for the noninvasive determination of peripheral outflow and flow disturbances in the extremities of human beings includes at least one light transmitter for directing light onto the skin of the subject under test and at least one light receiver for receiving reflected radiation and an evaluation and read-out circuit for ascertaining the temporal course of the blood outflow or inflow in the veins by measuring the changes in light reflection.

U.S. Pat. No. 5,360,005 to Wilk discloses a medical diagnostic method that comprises the steps of automatically sensing an acoustic vibration to an electrical signal, and converting the amplified electrical signal to an acoustic pressure wave. The steps of sensing and converting the sensed acoustic vibration to an electrical signal are implemented by operating an acoustoelectric transducer in a hand held device, and the method further comprises the step of holding the hand held device against a skin surface of the person.

U.S. Pat. No. 5,365,937 to Reeves et al. discloses a sensing device for capturing acoustic heart sounds. The sensing device has a diaphragm formed from a piezoelectric transducer material that generates excitation signals in response to acoustic and vibratory energy outputs. The sensing device includes metallization layers on the diaphragm for receiving and transmitting the excitation signals to an output display device via associated electrical contacts and electrical leads and also includes a layer of adhesive material for coupling the sensing device to the subject.

In taking noninvasive measurements of the human body, it is also know that array based measurements are ideal for situations where the signal-to noise ratio is small, such as energy emissions in the human chest. It is also found, however, that the ribs can physically block these emissions or alter them by causing scattering of the wave (energy) field.

SUMMARY OF THE INVENTION

An object of the present invention is to noninvasively measure energy emissions in the human chest with minimal interference from the surrounding ribs.

It is a further object of the invention to provide an array based measurement system that is reconfigurable from patient to patient so that it will fit various people with different size ribs and rib separations.

The device of the present invention is comprised of several linear sensor arrays placed in a nearly parallel arrangement. All the linear arrays are attached to two flexible rods and can slide along each rod. The method of attachment is a slider with a butterfly screw, which enables the spacing between each linear array to be adjusted to fit individual patients. Each array contains ten individual sensing elements. The rods are flexible so that the entire unit will conform to a person's chest, regardless of the amount of curvature. The linear arrays are designed to be placed between the ribs of a human so that chest signals can be measured with minimal interference from the rib cage. Additionally, there is enough tolerance in the array placement to locate each array slightly out of parallel to accommodate a patient whose ribs are not exactly parallel.

This device is an array based measurement system that minimizes the effect of rib interaction on the space-time field of the human thorax. This array-based measurement system is noninvasive in order to minimize patient risk.

BRIEF DESCRIPTION OF THE DRAWINGS

Other objects, features and advantages of the present invention will become apparent upon reference to the following description of the preferred embodiments and to the drawing, wherein corresponding reference characters indicate corresponding parts in the drawing and wherein:

The FIGURE is a schematic view of a preferred embodiment of the device of the present invention.

DETAILED DESCRIPTION OF THE PREFERRED EMBODIMENT

Referring to the FIGURE, the device of the present invention includes parallel spaced longitudinal rods 10 and 12 that are preferably vertically oriented. Longitudinal rods 10 and 12 can be made from soft metal or another material that can be bent to conform with a patient's chest. Longitudinal rod 10 has an upper terminal mounting bracket 14 and a lower terminal mounting bracket 16. Longitudinal rod 12 has upper mounting bracket 18 and a lower mounting bracket 20 on its opposed terminal ends. A rigid peripheral frame 22 is provided and is made up of an upper horizontal section 24, a lower horizontal section 26 and opposed space parallel sections 28 and 30. (Frame sections 24, 26, 28 and 30 can have a minor curve as necessary to conform to the patient's body.) A flexible sensor support 32, which is preferably a malleable material such as a soft metal or a thermoplastic material, extends transversely between the longitudinal rods 10 and 12. This malleable material should be capable of deforming and retaining the deformed shape to conform with a patient's body. On longitudinal rod 10, the flexible sensor support 32 has a peripheral attachment structure 34, which is secured with a butterfly screw or hinge 36. The peripheral attachment structure 34 can be a collar or some other positionable structure known in the art. On longitudinal rod 12, the flexible sensor structure 32 is attached by a peripheral attachment structure 38 secured by a butterfly screw or hinge 40. Butterfly screws or hinges 36 and 40 may be loosened to allow the flexible sensor support 32 to be moved up or down on the flexible rods 10 and 12 to avoid interference from the patient's ribs. Flexible sensor support 32 can be positioned horizontally or at an angle by adjusting peripheral attachment structures 34 and 38.

On the flexible sensor structure 32 there is a linear array of sensors 42 arranged in spaced transverse relation. This array of sensors 42 is made up of sensors 44, 46, 48, 50, 52, 54, 56, 58, 60 and 62. The individual sensors can be strain gages, accelerometers, velocimeters, stress sensors, pressure sensors, or displacement measuring instruments.

Once the array is placed on the patient, the sensors are turned on and the space-time field at the sensors is measured. Using signal processing techniques, the origin of the energy emissions can be determined. Beneath flexible sensor support 32 there is a flexible sensor support 64 that is positioned between the longitudinal rods 10 and 12 in a spaced relation to flexible sensor support 32 at an angle 96 which is preferably between 0 degrees and 30 degrees. The flexible sensor support 64 is attached to the longitudinal rod 10 by peripheral attachment structure 66 secured by butterfly screw or hinge 68. The flexible sensor support 64 is attached to longitudinal rod 12 on its opposed end by peripheral attachment structure 70 secured by butterfly screw or hinge 72. The flexible sensor support 64 has a linear sensor array 74 which has a plurality of transversely spaced sensors 76, 78, 80, 82, 84, 86, 88, 90, 92 and 94. Flexible support 64 is not required to be parallel to flexible support 32, and is disposed thereto at on acute angle 96, which is preferably from 0 degrees to 30 degrees. This arrangement may allow placement to better avoid the patient's ribs. Butterfly screws or hinges 68 and 72 may be loosened to allow the flexible sensor support 64 to be moved up or down on the flexible rods 10 and 12 for the purpose of avoiding interference from the patient's ribs.

Beneath the flexible sensor support 64 there is another flexible sensor support 98 which is horizontally disposed. Like support 32 and support 64, flexible sensor support 98 can be positioned at an acute angle to the horizontal. This flexible sensor support 98 is attached to longitudinal rod 10 by peripheral attachment structure 100 secured by butterfly screw or hinge 102. At its opposed end, flexible sensor structure 98 is attached to longitudinal rod 10 by peripheral attachment structure 104 that is secured by butterfly screw or hinge 106. On the flexible sensor support 98 there is a linear sensor array 108 which is made up of transversely spaced sensors 110, 112, 114, 116, 118, 120, 122, 124, 126 and 128. Butterfly screws or hinges 102 and 106 may be loosened to allow the flexible sensor support 98 to be moved up or down on the flexible rods 10 and 12 for the purpose of avoiding interference from the patient's ribs.

An optional hinged door (not shown) can be attached to the peripheral frame 22. The door can shield the sensors from acoustic and electromagnetic interference from the outside environment. Additionally, tracing paper (not shown) can be placed between the door and the sensors so that the sensor location can be marked and the final location of the sensor can be measured for each individual patient.

It will be appreciated that the reconfigurable array of the present invention allows effective placement and location of sensors. The main advantage of using this new method is that the measurements contain minimal interference from the rib cage. Additionally, it is a noninvasive procedure that involves no patient risk. Invasive procedures such as angiograms could be used instead of this noninvasive method. Invasive procedures involve significant risk of injury to the patient.

While the present invention has been described in connection with the preferred embodiment of the FIGURE, it is to be understood that other similar embodiments may be used or modifications and additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A device for noninvasively measuring energy emissions in the human chest comprising:
   first and second spaced longitudinal flexible supports;
   at least one transverse support means having a first terminal end and a second terminal end, the first terminal end being positioned on the first spaced longitudinal flexible support and the second terminal end being positioned on the second spaced longitudinal flexible support; and
   a plurality of sensor means positioned in a spaced array on the transverse support means wherein said plurality of sensor means comprise sensors selected from strain gauges, accelerometers, velocimeters, stress sensors, pressure sensors and displacement sensors.

2. The device of claim 1 wherein said at least one transverse support comprises a plurality of transverse support means and, each of the transverse support means is longitudinally spaced from said other transverse support means.

3. The device of claim 2 wherein each of the transverse support means can be angularly disposed with respect to the other of said plurality of transverse support means.

4. The device of claim 1 wherein the transverse support means is longitudinally displaceable on the first and second longitudinal flexible supports.

5. The device of claim 1 wherein the first and second spaced longitudinal flexible supports are respectively first and second flexible rods.

6. The device of claim 5 wherein the first and second terminal ends are disposed on the first and second flexible rods by first and second collars.

7. The device of claim 6 wherein the first and second collars are equipped with fastening means which may be loosened to allow each collar to be independently moved along the first and second flexible rods.

8. The device of claim 1 further comprising:
   a rigid frame; and
   said first and second spaced longitudinal flexible supports each having two opposed ends, and each said end being mounted to said rigid frame.

9. The device of claim 8 wherein said rigid frame is curved for conforming with the human chest.

* * * * *